United States Patent
Kleinman (10) Patent No.: US 8,343,214 B2
(45) Date of Patent: Jan. 1, 2013

(54) APPARATUS FOR THE TREATMENT OF CATARACT

(75) Inventor: David Maxwell Kleinman, Rochester, NY (US)

(73) Assignee: Cateract Innovations LLC, Rochester, NY (US)

( * ) Notice: Subject to any disclaimer, the term of this patent is extended or adjusted under 35 U.S.C. 154(b) by 438 days.

(21) Appl. No.: 12/581,152

(22) Filed: Oct. 18, 2009

(65) Prior Publication Data
US 2010/0100194 A1    Apr. 22, 2010

Related U.S. Application Data (60) Provisional application No. 61/106,876, filed on Oct. 20, 2008.

(51) Int. Cl.
*A61F 2/16* (2006.01)

(52) U.S. Cl. ........ 623/4.1; 623/6.12; 623/6.56; 606/107

(58) Field of Classification Search .................... 623/4.1, 623/6.11–6.12, 6.18, 6.56; 606/107
See application file for complete search history.

(56) References Cited

U.S. PATENT DOCUMENTS

| | | | |
|---|---|---|---|
| 2,555,076 A * | 5/1951 | Crossley ................... 606/107 |
| 3,942,519 A * | 3/1976 | Shock ...................... 606/128 |
| 4,301,802 A | 11/1981 | Poler |
| 4,530,117 A * | 7/1985 | Kelman ..................... 623/6.12 |
| 4,710,194 A | 12/1987 | Kelman |
| 4,862,885 A * | 9/1989 | Cumming ................... 606/107 |
| 4,955,904 A | 9/1990 | Atebara et al. |
| 5,021,043 A * | 6/1991 | Becker et al. ................ 606/192 |
| 5,312,413 A * | 5/1994 | Eaton et al. ................. 606/107 |
| 5,653,715 A * | 8/1997 | Reich et al. ................. 606/107 |
| 5,702,441 A * | 12/1997 | Zhou ........................... 128/898 |
| 5,772,667 A | 6/1998 | Blake |
| 5,941,886 A * | 8/1999 | Feingold .................... 606/107 |
| 6,068,642 A * | 5/2000 | Johnson et al. ............. 606/180 |
| 6,899,424 B2 | 5/2005 | Miller et al. |
| 7,435,255 B1 * | 10/2008 | Rao .............................. 623/1.42 |
| 8,114,095 B2 * | 2/2012 | Rathert ....................... 606/107 |
| 8,162,953 B2 * | 4/2012 | Dishler et al. .............. 606/107 |
| 2002/0055776 A1 * | 5/2002 | Juan et al. ................... 623/6.12 |
| 2003/0229303 A1 | 12/2003 | Haffner et al. |
| 2006/0155300 A1 * | 7/2006 | Stamper et al. ............. 606/107 |
| 2006/0190003 A1 * | 8/2006 | Boukhny et al. ........... 606/107 |
| 2006/0247660 A1 | 11/2006 | Perez |
| 2008/0114373 A1 * | 5/2008 | Rathert ....................... 606/107 |
| 2009/0182421 A1 * | 7/2009 | Silvestrini et al. .......... 623/6.13 |

OTHER PUBLICATIONS

PCT International Search Report and Written Opinion for International Application No. PCT/US 09/61206; Date of Mailing Feb. 4, 2010. 9 pages.

* cited by examiner

*Primary Examiner* — Paul Prebilic
(74) *Attorney, Agent, or Firm* — Patent Technologies, LLC; Robert D. Gunderman, Jr.

(57) ABSTRACT

A method and related apparatus to treat a cataract where the cataractous lens is pierced and the resulting opening is mechanically maintained using a lens system device such as a pinhole device, expandable tubular lens, a stent or similar small diameter device, some of which are capable of supporting a secondary intraocular lens. The resulting passageway or lumen created in the cataractous lens allows visible light to better reach the retina, thus improving vision. This lens system device that can be placed into an in situ cataract provides for a much simpler surgical technique and reduces related pre and post operative procedures and potential complications. Intraocular lenses may also be used in concert with this invention. The apparatus and technique can be applied to humans as well as animals.

15 Claims, 13 Drawing Sheets

APPARATUS FOR THE TREATMENT OF CATARACT

CROSS REFERENCE TO RELATED PATENT APPLICATIONS

This application claims priority to U.S. Patent Application Ser. No. 61/106,876 filed Oct. 20, 2008 entitled "Apparatus and Method For The Treatment of Cataract" by Dr. David M. Kleinman of Rochester, N.Y.

BACKGROUND OF THE INVENTION

1. Field of the Invention

This invention relates generally to surgery of the eye, and more particularly to an apparatus and a method for the treatment of cataract.

2. Description of Related Art

Cataract is the leading cause of blindness in the world. There are currently over 100 million people in the world that have cataracts that interfere with visual function. In addition, there are currently approximately 22 million people in the world who are completely blind from cataracts. The vast majority of these patients live in developing countries. Despite modern surgical techniques, the rate of cataract blind increases annually. The prevalence of bilateral cataract blind is currently increasing by 1.5 million people per year. There are seven million cataract surgeries performed annually, but the fact that ophthalmologists cannot remove the backlog of bilateral cataract blind or even keep up with the rates of new cataracts generally is clear evidence that a new methodology to deal with developing world cataracts is required.

Pediatric cataract is a devastating problem world wide, and its treatment is very challenging. The disability and economic burden on families, communities, and countries based on the combination of pediatric and adult cataract is staggering.

Cataracts are an opacification of the natural human lens. Current methods of cataract treatment include removal of the lens, and refractive correction. Oftentimes, an intraocular lens is used. Historically, the lens could be couched with a needle. There are no pharmacological treatments for cataract blind. It is purely a surgical disease. Extracapsular cataract extraction is a very effective method for treating cataract blind. Once the cataractous lens is removed, more light will enter the eye; however, a method to focus the light (except in the rare case of very high myopes) is required. Either spectacles or a precise and calculated power of intraocular lens is required. To choose the correct power intraocular lens, biometry and keratometry are required. These technologies are often not available in the developing world, and as a consequence, standard powered lenses are implanted in the hope that most people will see substantially better.

The current invention not only describes a novel apparatus and method for treating millions of individuals blind from cataract, and in some embodiments also reduces the need for precise refractive correction after cataract treatment.

It is thus an object of the present invention to provide an apparatus and method for treating cataract that can be performed in locations without extensive cataract treatment support infrastructure. It is another object of the present invention to provide an apparatus and method for treating cataract that can be performed in locations with fewer specialized practitioners. It is another object of the present invention to provide an apparatus to treat cataract. It is yet another object of the present invention to provide an apparatus to assist with a novel method of treating cataract.

BRIEF SUMMARY OF THE INVENTION

In accordance with the present invention, there is provided an apparatus for treating cataract of an eye having a surgical tool formed with an angle to allow entry of the surgical tool through the peripheral cornea of the eye, the angle creating a longer operative end of the surgical tool and a shorter surgical end of the surgical tool; the shorter surgical end of the surgical tool having a sharp tool for penetration of a cataractous lens of the eye; a lens system device, or lumen creation system, contained within the surgical tool; and an advancing or guiding structure attached to the lens system device and further disposed within the surgical tool. The present invention includes mechanisms to ease placement of the lens system device to into the cataract and to aid in the release of such a placement apparatus from the deployed lens system device.

The foregoing paragraph has been provided by way of introduction, and is not intended to limit the scope of the invention and its various embodiments described, depicted, or envisioned herein.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims, and the attached drawings.

DESCRIPTION OF THE PREFERRED EMBODIMENTS

For a general understanding of the present invention, reference is made to the drawings. In the drawings, like reference numerals have been used throughout to designate identical elements.

The present invention and the various embodiments described or suggested herein rely on a surgical technique where the natural lens of the eye is pierced and the resulting opening is mechanically retained using a device that operates in ways that may be similar to cardiovascular stenting technologies. The resulting passageway, lumen, or lens system created in the natural or cataractous lens allows light to reach the retina, thus improving vision. The resulting passageway through the natural lens is made through a diameter less than the diameter of the natural lens. The use of this lens system device with or without the pinhole principle provides for a much simpler surgical technique and reduces related pre and post operative procedures.

The apparatus and method of the present invention may involve human cases, and also may be critically important in pediatric cases, as light will be in focus on the retina, reducing the need for complex cataract surgery followed by contact lenses or glasses in infants, and thus also may play a role in preventing ambylopia. In addition, veterinary cases of cataract such as those which develop in dogs, cats, horses, and the like, may benefit from the apparatus and method of the present invention and the various embodiments described or envisioned herein.

Turning now to the drawings, both an exemplary surgical device, as well as related devices and methods, will be described using the drawings attached herein.

Figure 1:
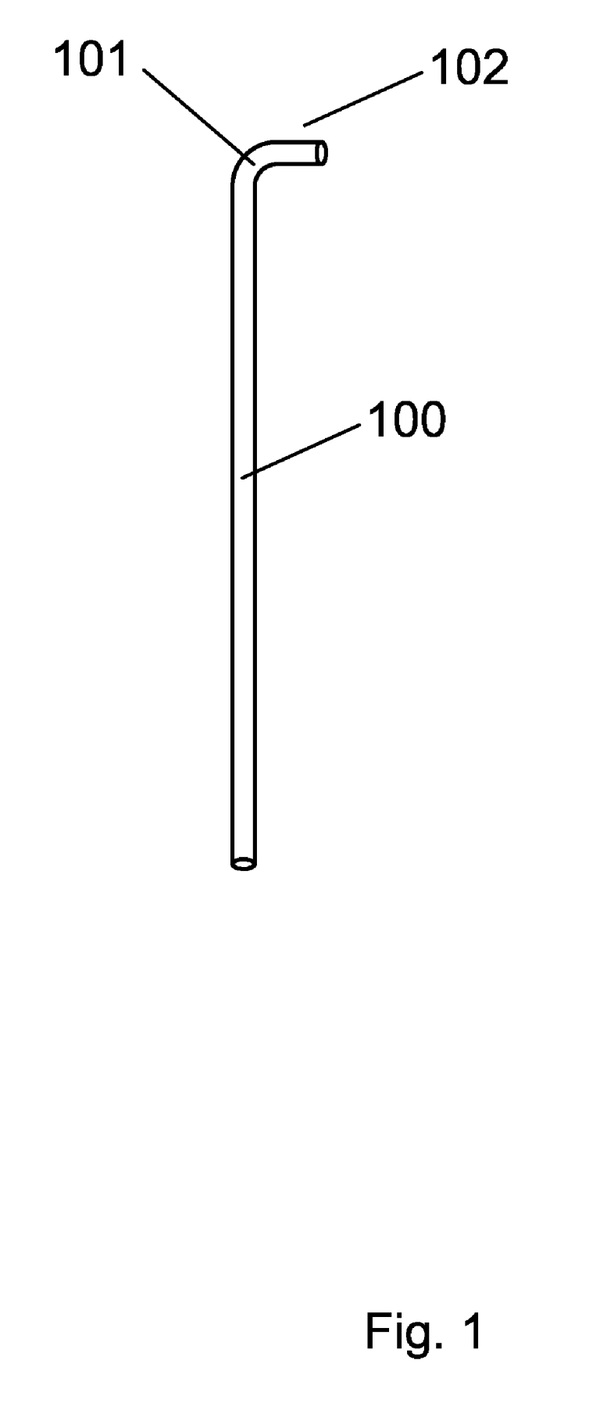
FIG. 1 depicts a surgical tool for the treatment of cataract.

In FIG. 1, a surgical tool for the treatment of cataract is depicted. The surgical tool 100, in one embodiment, is essentially a hollow tube such as a cannula or related structure made from stainless steel, titanium, plastics, biocompatible polymers, or other material that is used to fabricate surgical instruments. The surgical tool 100 contains an angle 101. The angle is used to facilitate the method of the present invention, as will be further described herein. The angle may be ninety (90) degrees, as depicted in FIG. 1, or it may be within approximately sixty (60) degrees greater or less than ninety (90) degrees. The surgical tool 100 may, in some embodiments of the present invention, contain a sharp edge or other incision or cutting tool, such as, for example, a trocar, to assist with the method of the present invention. The sharp tool would be located at 102.

Figure 2:
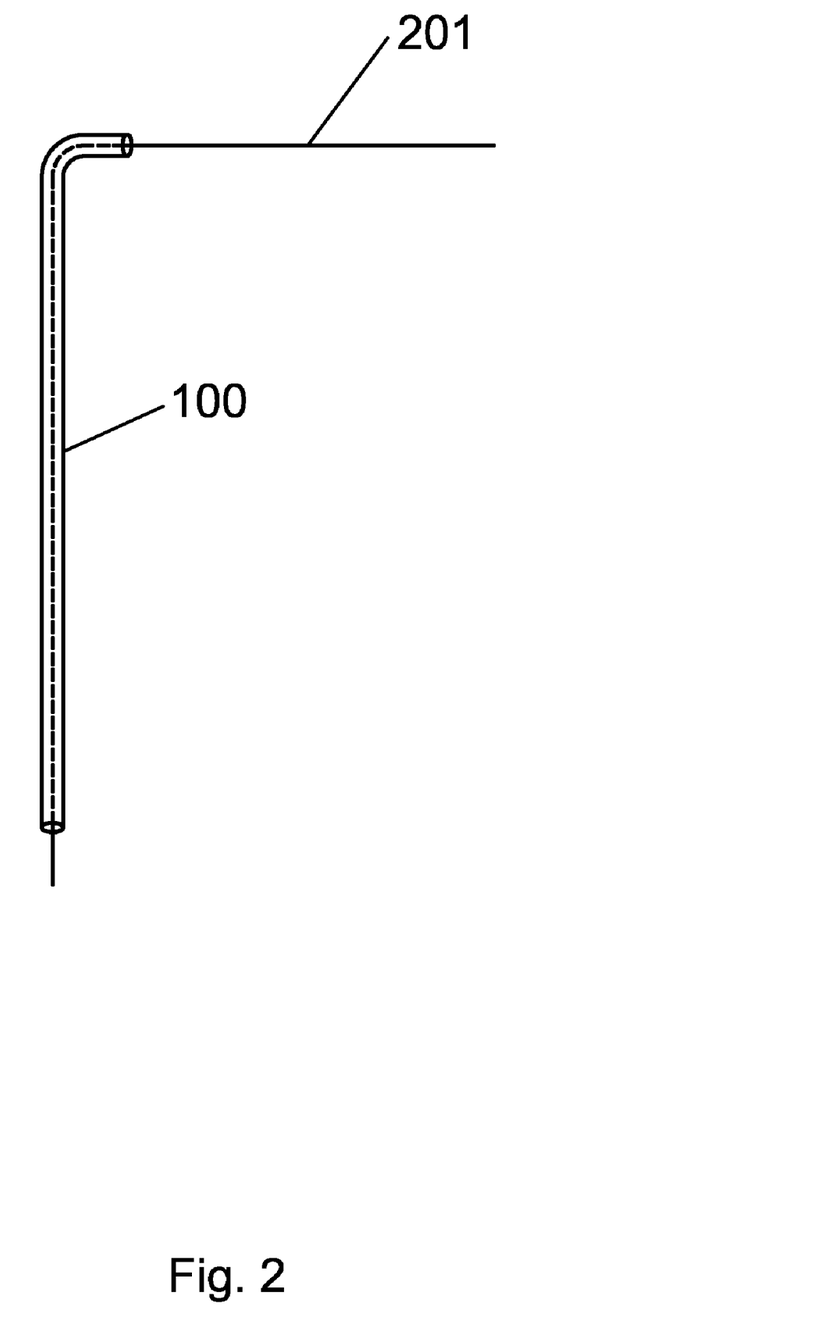
FIG. 2 depicts a surgical tool for the treatment of cataract with a guide wire disposed within and through the surgical tool.

FIG. 2 further depicts the surgical tool 100 with a guiding structure 201 disposed within the surgical tool 100. The guiding structure, or guide wire in this example 201 must be capable of traveling through the angle 101 or conveying force through the angle, and must be of sufficient rigidity to support the piercing of the natural lens with its related cataract. Materials for the guide wire may include stainless steel, titanium, Kevlar, encapsulated glass (fiber optic material), and the like. Materials for the guiding structure may include metals, plastics, polymers, and the like. The guiding structure term is nomenclature that may include, but is not limited to, a guiding or lens system advancing structure, and also serves to reference a system that would deploy through the cannula for the purpose of piercing the cataractous lens allowing for the placement of the lens system device or stent or second permanent hollow cannula, lens, or lens system device that remains in the lens, or the guiding structure may be integral to, part of, or built into the surgical tool. The guiding structure may be one and the same as the surgical tool in some embodiments. The guiding structure may also refer to a method for advancing the lens system device into the cataractous lens. Heat, ultrasound, laser, or other electromechanical processes may be deployed at the tip to ease the penetration of the system through the lens. The material or part of it, such as, for example, the leading or trailing ends, may also be biodegradable material such as Polyglycolic acid polymers.

Figure 3:
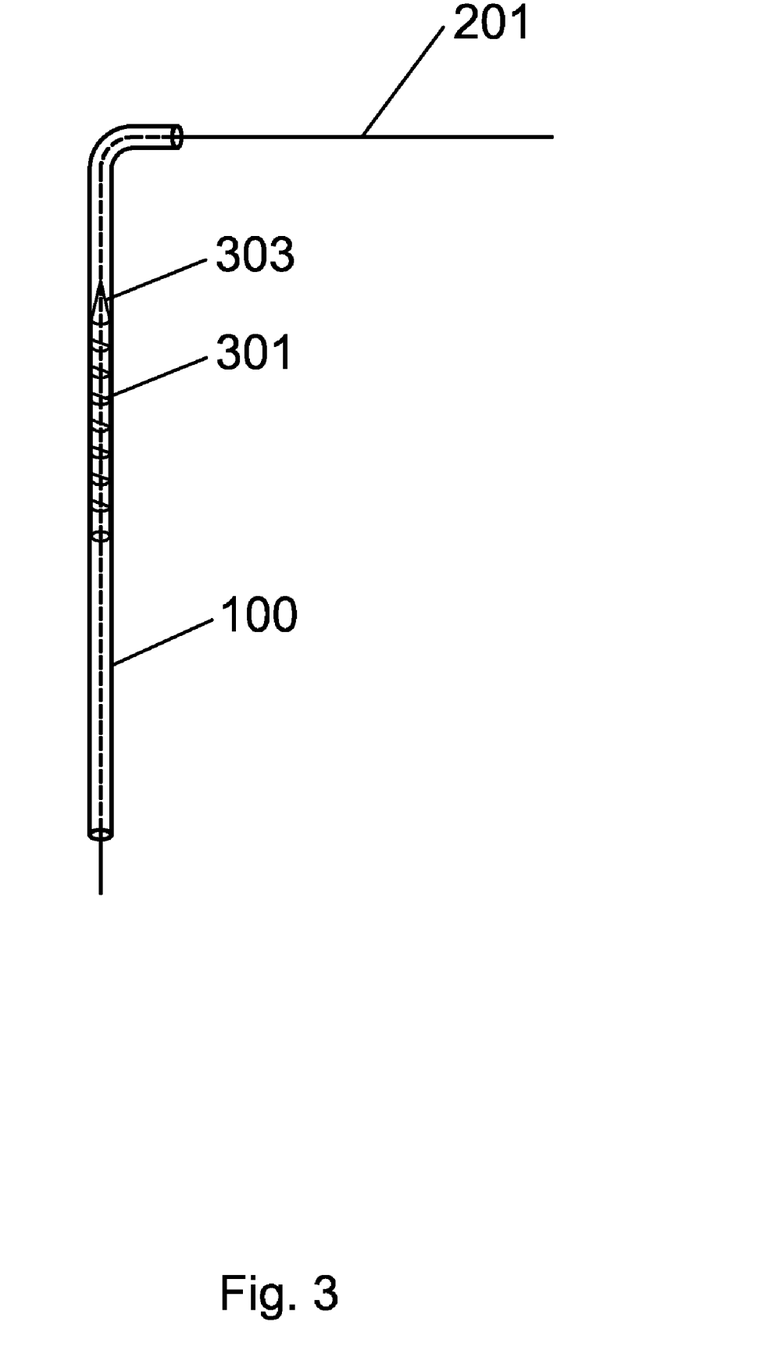
FIG. 3 depicts a surgical tool for the treatment of cataract with a guide wire and lens system device installed.

In FIG. 3 a lens system device 301, such as, for example a stent, is depicted within the surgical tool 100. The stem may be similar in structure and concept to a cardiac stent, but will be dimensioned to accommodate the procedure described herein. The lens system device 301 is a tubular sleeve capable of expansion. An example of a cardiac stent is disclosed in U.S. Pat. No. 7,435,255 to Rao entitled "Drug Eluting Stent and Methods of Making", the entire disclosure of which, and the references cited therein, are incorporated in their entirety herein. The lens system device 301 may be fabricated from a metallic material such as stainless steel, platinum, titanium, tantalum, nickel-titanium, cobalt-chromium, and alloys thereof. In addition, the lens system device 301 may further contain drugs that are carried in a polymeric coating or sleeve that may or may not be loaded with at least one therapeutic drug. Suitable polymers for the lens system device, with or without drug loading include, for example, poly(methyl methacrylate) ("PMMA"), poly(ethylene-co-vinyl alcohol) ("EVAL"), poly(butyl methacrylate) ("PBMA"), polyglycolic acid ("PGA"), poly(L-lactic acid) ("PLLA"), woven polymers, silicones, hydrogels, copolymers and blends thereof, as well as various nanomaterials such as carbon nanotubes and the like, or other polymers used for biocompatible coatings, linings, or with drug delivery capabilities familiar to those skilled in the art. The lens system device may also be made from a hydrophilic material that expands upon placement in an aqueous environment such as an eye. Suitable hydrophilic materials may include, but are not limited to, poly(2-Hydroxyethylmethacrylate) (pHEMA), hydroxyethyl methacrylate (HEMA), hydrophilic acrylic, hydrogels, hydrophilic polymers, fluorocarbon-sulfone. Thus, a dehydrated transparent hydrophilic polymer would expand over time once placed in position through the cataract. Also depicted in FIG. 3 is a taper 303 that is an integral part of, or a detachable part of, the lens system device 301. The taper 303 allows the lens system device 301 to travel and insert into the created lumen in the natural lens. This aspect to the device may also be capable of transmitting heat, ultrasound, laser, or other electromechanical energies to ease placement through the cataractous lens. The taper 303 may be present in some embodiments of the present invention, and may be absent from the lens system device 301 in other embodiments of the present invention. The taper may, in some embodiments of the present invention, may be biodegradable, or threaded. In some embodiments of the present invention, the lens system device 301 may be surrounded by a component that would prevent lens material from entering the patent space opened by the stent or lens system device. The component that surrounds the lens system device to keep the lens material out could be made from DACRON® (polyethylene terephthalate fibers), GORE-TEX® (expanded polytetrafluoroethylene), Nylon, or other biodegradable or non-biodegradable materials. This outer coating, or the entire lens system device could be made from intraocular lens material such as acrylic, PMMA, or silicon. There also may be an intraocular lens contained in the lens system device, or deployed into it in an additional step. The diameter of this lens system device would range from less than 1 mm (0.19 mm minimum) up to 5 mm after expansion. The lens system device may be completely embedded in or surrounded by the intraocular lens material or polymer that keeps lens material out of the patent space through the lens. The lens system device may contain a tubular, expandable, foldable or non foldable IOL or synthetic lens material in its center. The lens power would range from −50 to +50 diopters, but would, in one embodiment be +16 to +20 dioptrs. The lens system device may expand to 4 mm in one embodiment, but could function with diameters of between 2 and 5 mm. The lens system device or stent may expand to 4 mm in one embodiment, but contain in the midpoint, a metal plate with a smaller opening (pinhole) in the range from 0.10 mm to 3 mm. In one embodiment, an opaque covering is placed with the lens system device that extends outside the anterior opening for 360 degrees around reaching a diameter up to 8 mm but it could be as little as 1 mm wider than the central opening.

In use, the cataractous lens of a patient is pierced directly in the visual axis with a sturdy material or device such as a wire, for example the guide wire 201, with or without an accompanying flexible or rigid catheter, and a small stent or other small or medium sized diameter device is placed in the defect created. The new space created in the cataractous lens is maintained by a device such as a metal stent (titanium or other metals), or plastics (silicones, hydrogels or PMMA or others), or a lens system device or tubular lens or other biocompatible material. The stent or lens system device may be surrounded by a biocompatible shell such as Dacron®, Gore-Tex®, acrylic, PMMA, silicone or any non absorbable or absorbable or biodegradable material to maintain the patency of the newly created opening and to ensure lens material does not enter into the full thickness hole in the lens (especially in the case of wire stents, but other scenarios as well). Polymer coatings may be hydrophilic or hydrophobic. The diameter of the passageway or lumen or opening is typically 1.5 mm. to 3.5 mm., but it can be smaller or larger. The tight fit of the lens system device 301, stent, lumen maintainer, tubular lens, or pinhole device adjacent to the anterior or posterior capsule will prevent dissipation of lens material into the anterior or posterior segments: the lens capsule will be snug against the device. This procedure will not prevent traditional types of cataract extraction in the future. Light will go through the small aperture, lens system device, tubular lens, expandable tubular lens, tubular lens made from hydrogel polymers, or in some embodiments a pinhole, and focus on the retina, because of A) refractive correction by the patient. B) an intraocular lens in the system, C) the pinhole principal regardless of the refractive error of the eye, or D) the focus may be suboptimal, but the vision provided will be superior to the vision with the cataract in place. In one embodiment, the vision will essentially be aphakic quality. In this scenario, there may be an opening, passageway, or lumen between 3 and 5 mm in diameter through the cataract. A secondary anterior chamber, or intraluminal lens may also be placed either in front of or inside the lumen to correct refractive error. The method involves entering the peripheral cornea, opening through the lens a significant passageway for light, and maintaining its patency with a specially designed device such as the lens system device 301. The lens system device could be of polymeric construction, for example, PMMA, silicone, or acrylic construction, hydrogel construction, or titanium or other metals or other polymers or combinations thereof, possibly including other materials that are used to treat cataracts or manufacture stents or intraocular lenses. To gently pierce the cataract, a mechanized system may be required, such as using ultrasound energy, laser, heat, or other mechanical means to allow the passage of the guiding system and or stent through the cataract. In one embodiment, a supporting instrument may be passed through the pars plana to stabilize the lens for the procedure. Methods for stabilizing the lens when the surgical tool and/or guiding structure is detached from the lens system device or stent or removed from the eye are included as embodiments of the present invention and may include mechanical or other methods of release systems. Other embodiments of the present invention use a screw type technology to pierce and drive a guiding structure (with or without an accompanying flexible or rigid catheter, stent, balloon, or expandable lens system) or other structure through a cataractous lens in a human or animal eye to create a clear space or tunnel for light to pass through to preserve or improve sight. In one embodiment the lens system device or stent will be flexible enough to make the turn through angle 101 in FIG. 1. In one embodiment, the rigidity of the stent is supplied by rings or spiral material inside the stent. The use of this technology is applicable and useful in human or animal lenses of any density and brunescence or any type of cataract including but not limited to congenital, acquired, traumatic, nuclear, polar, cortical, posterior subcapsular, infectious, post operative, inflammatory. In the case of some cataracts penetration of the lens material will be easier (pediatric or traumatic cataract) or more difficult (calcific, senile, or brunescent cataract). The system may be tunable so that less energy is used to penetrate one type of cataract versus another. In one embodiment of the present invention, a mechanized system is employed that imparts rotational energy to the guiding structure, stent components (all with or without threads), or both during the procedure to ease their passage into and through the cataractous lens. In other embodiments, electrical, electrocautery, thermal, laser, ionization, chemical, nuclear, or ultrasonic energy is used to aid in the penetration of the cataractous lens and/or for the placement of the stent or lens system device that is integral to this invention.

FIGS. 4 through 13 provide examples of the steps involved in the methods of the present invention, and also provide examples of how to use the surgical tool and related implantable device of the present invention. The examples provided in the figures are not to be construed as limitations of the present invention and its various embodiments described herein, but rather, are depicted to fully allow one skilled in the art to make and use the invention along with modifications, adaptations, and alterations, all being within the spirit and broad scope of the present invention as fully defined herein. FIGS. 4 through 13 depict a human eye, but the methods and apparatus of the present invention are equally well adapted to veterinary medicine.

Figure 4:
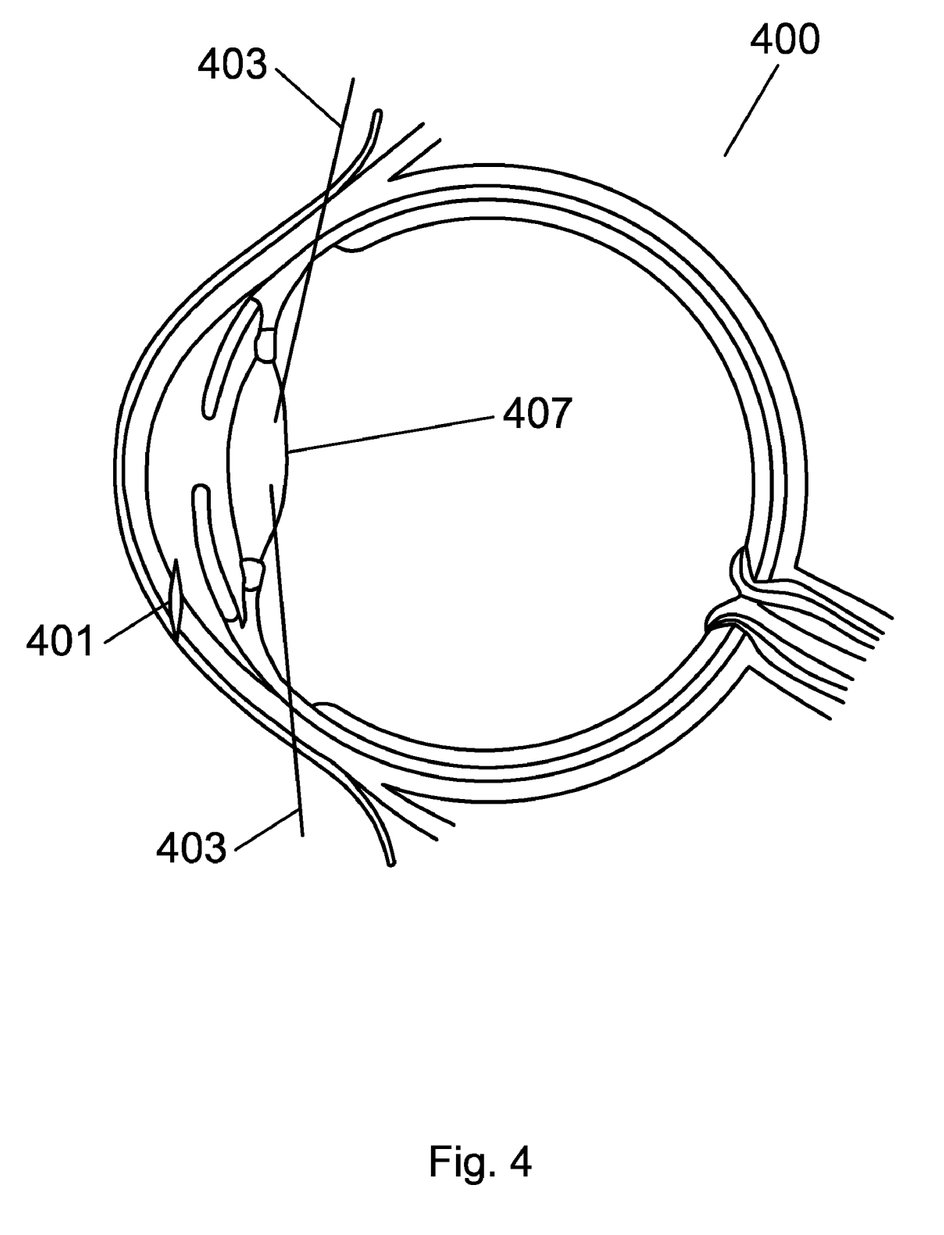
FIG. 4 is a cross sectional view of an eye showing the surgical incision.

In FIG. 4, an eye 400 is depicted. An incision 401 is made in the cornea, the diameter of the incision through the cornea can be between 0.25 mm. and 2 mm., being self sealing, but may be up to 6 mm., and may require surgical closure. In some embodiments of the present invention, a support structure or support structures 403 may be used to hold the lens in place during surgery. In some embodiments of the present invention, a polymer block is used that rests externally on the eye to stabilize it so that when the guiding structure and/or surgical tool (with or without an accompanying flexible or rigid catheter) and other related technologies are entered into the cornea, the eye is held steady to minimize the risk of injury through movement. Viscoelastic, or other viscous materials may be injected into the anterior chamber (and left in place or washed out) during the procedure to maintain the anterior chamber. Alternatively, a simple anterior chamber maintainer such as a needle or Lewicky cannula may be used to maintain the anterior chamber. The goal of the surgery is to place a hole and support structure (such as but not limited to a stent, lens system device, tubular lens, IOL, or lumen maintainer) through the cataractous lens 407, thus allowing light to enter the back of the eye to the retina, improving vision.

Figure 5:
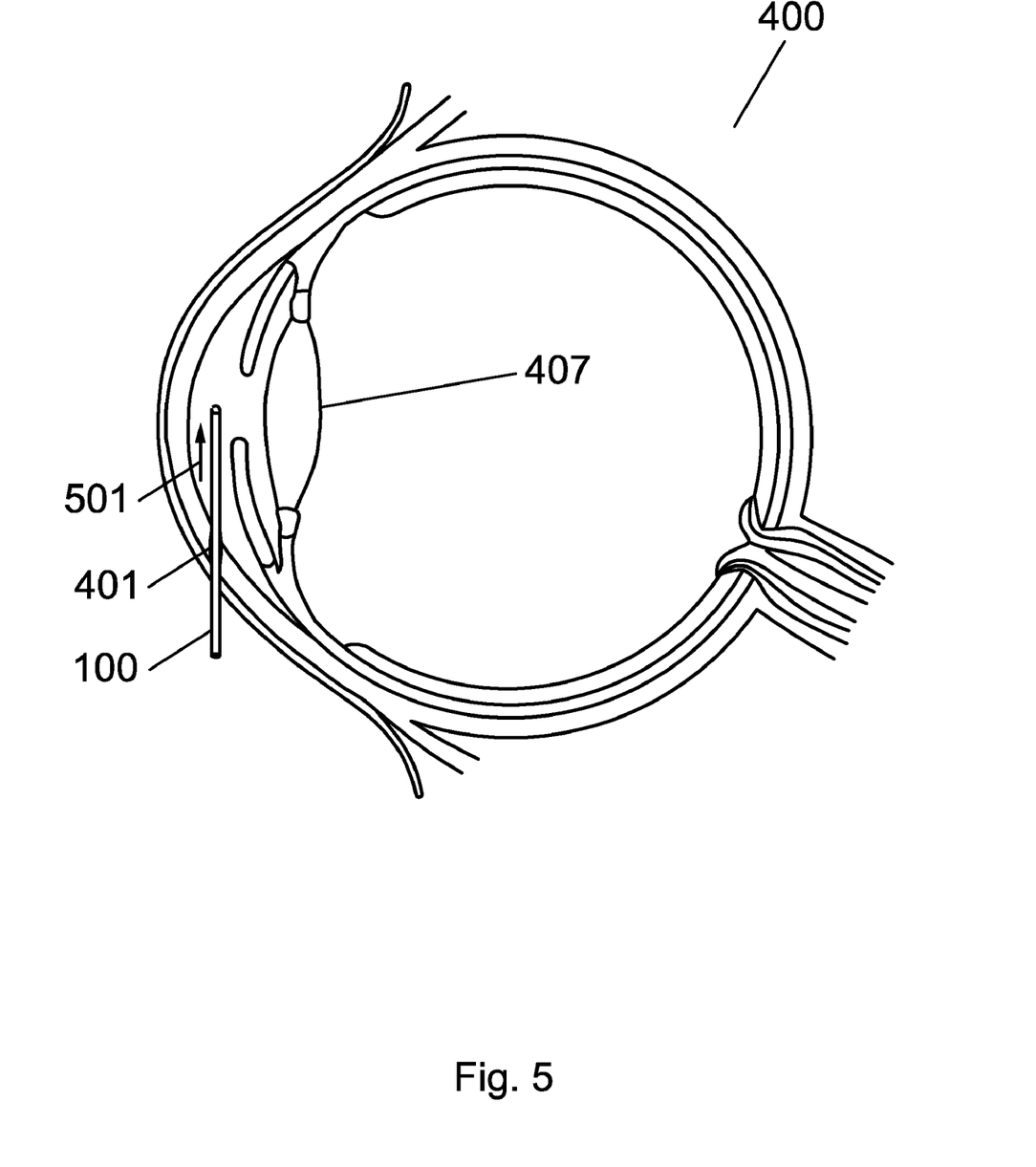
FIG. 5 is a cross sectional view of an eye showing the surgical tool entering the incision.
Figure 6:
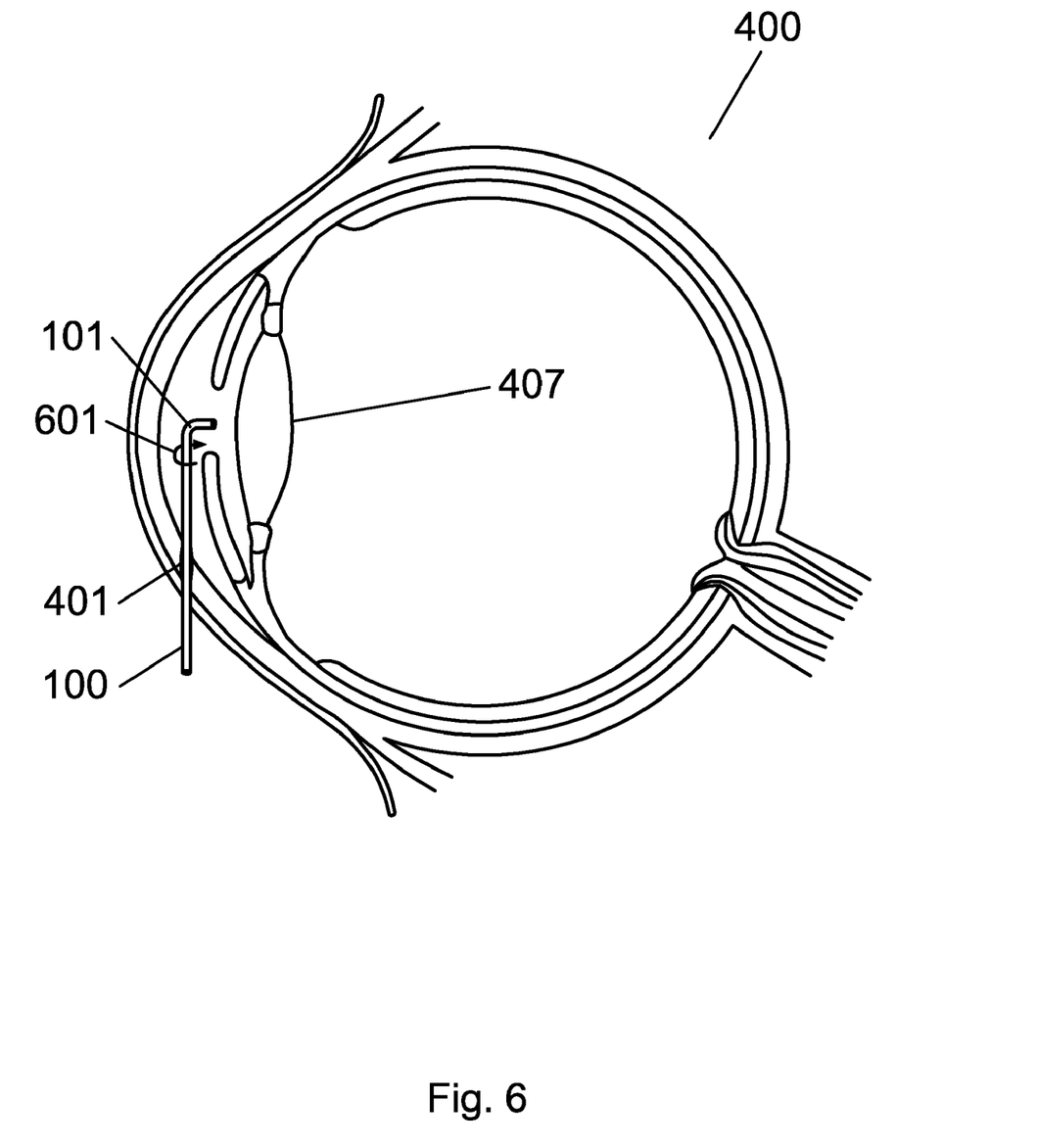
FIG. 6 is a cross sectional view of an eye showing the surgical tool being rotated into position.
Figure 7:
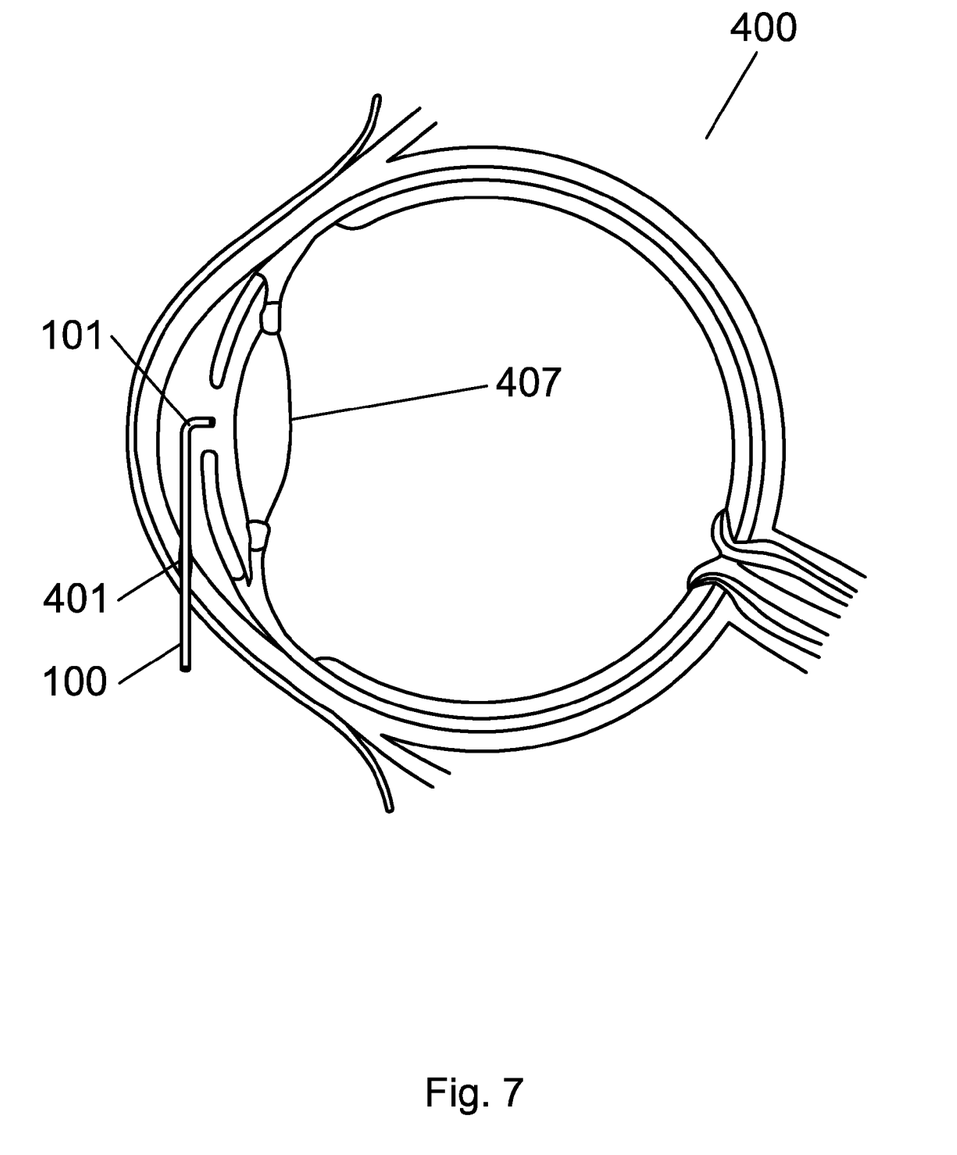
FIG. 7 is a cross sectional view of an eye showing the surgical tool in position.

FIG. 5 now depicts the surgical tool 100 entering the incision 401 in a linear direction of travel 501, as depicted by way of 501. Note that the surgical tool 100 is placed in such a way as to clear any and all obstructions. Once the surgical tool 100 is in a position where the guiding structure or guide wire (not shown in FIG. 6) may be directed toward the visual axis and center of the lens, the surgical tool 100 is rotated in a rotational direction of travel 601 such that a pinhole and related lens system device deployment may be made. FIG. 7 shows the surgical tool in the proper position after rotation.

Figure 8:
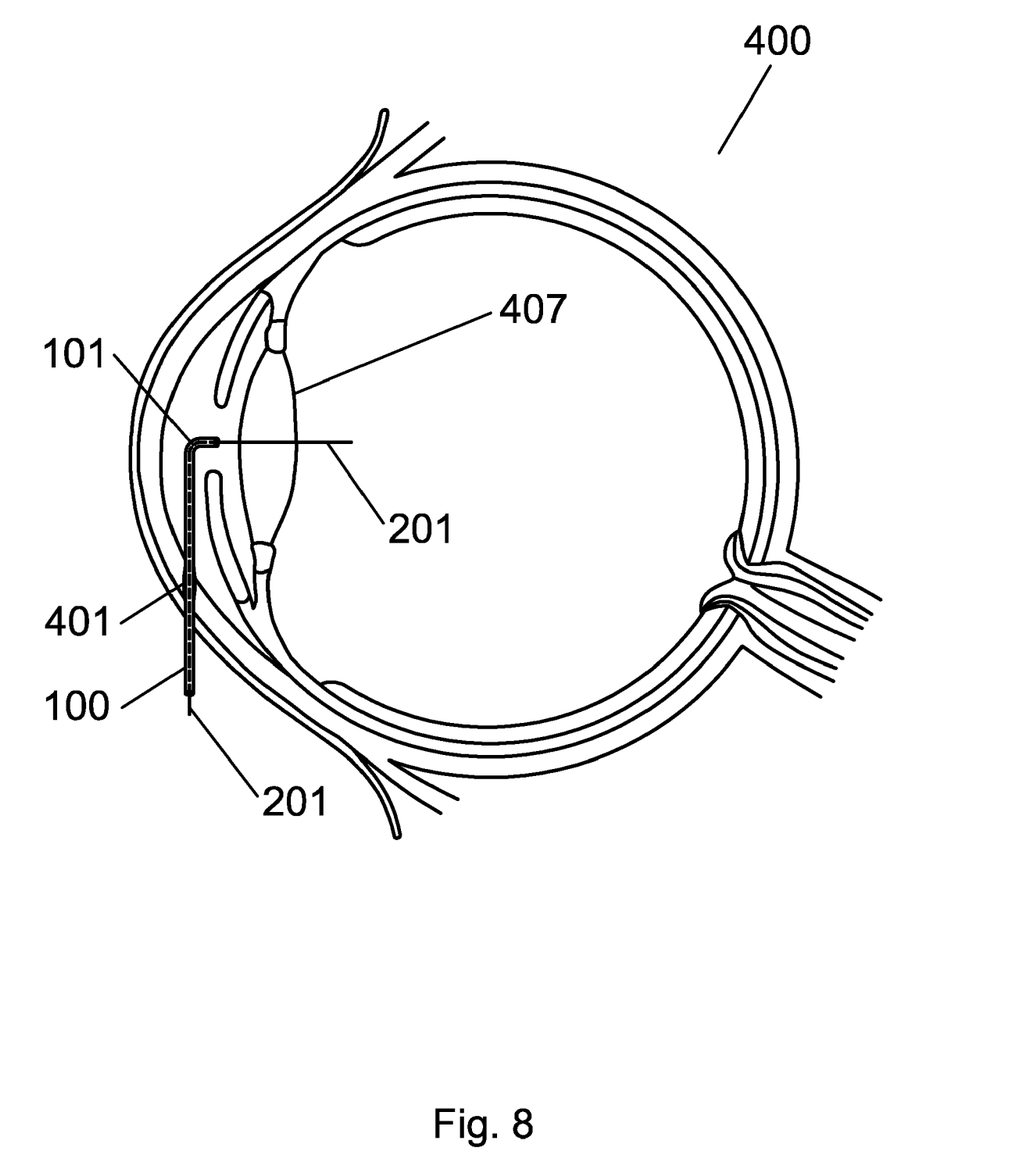
FIG. 8 is a cross sectional view of an eye showing the guide wire being deployed.

In FIG. 8, a guide wire or guiding apparatus 201 or similar rigid structure is inserted in the hollow of the surgical tool 100, passed through the hollow of the surgical tool 100, and allowed to exit the surgical tool 100 in such as a way as to create a pinhole, track, passageway or lumen through the lens. The guide wire or guiding structure 201 may include plastics, balloons, flexible wires, catheters, needles, hollow pipes, fiberoptic cables, rotational drills, ultrasound, electrocautery, lasers including femtosecond, continuous wavelength, ND YAG, and other methods to generate heat or other types of energy to pierce the anterior lens capsule and then the entire lens to create the opening through that lens. Any or all of these techniques may also be used to create a space for insertion of a guide wire and with or without similar methods for the passage of the ultimate cannula, stent, lens system (expandable lens in some embodiments) that eventually maintains the patent opening through the cataract. In some embodiments of the present invention, a fiberoptic cable or strand may be used to maintain patency of the opening, and, in some embodiments of the present invention, may be used to bypass a cataract. In some embodiments of the invention the lens device system or stent is passed over the guiding structure into the lens for its deployment, in other embodiments, the guiding structure and or guide wire may be passed into the lens simultaneously with the lens device system or stent, such that the guiding apparatus essentially allows for the positioning, deployment, and eventual release of the lens device system, expandable intraocular lens, stent, or lumen creation device. The guiding apparatus can be part of, or one in the same, as the surgical tool itself.

Figure 9:
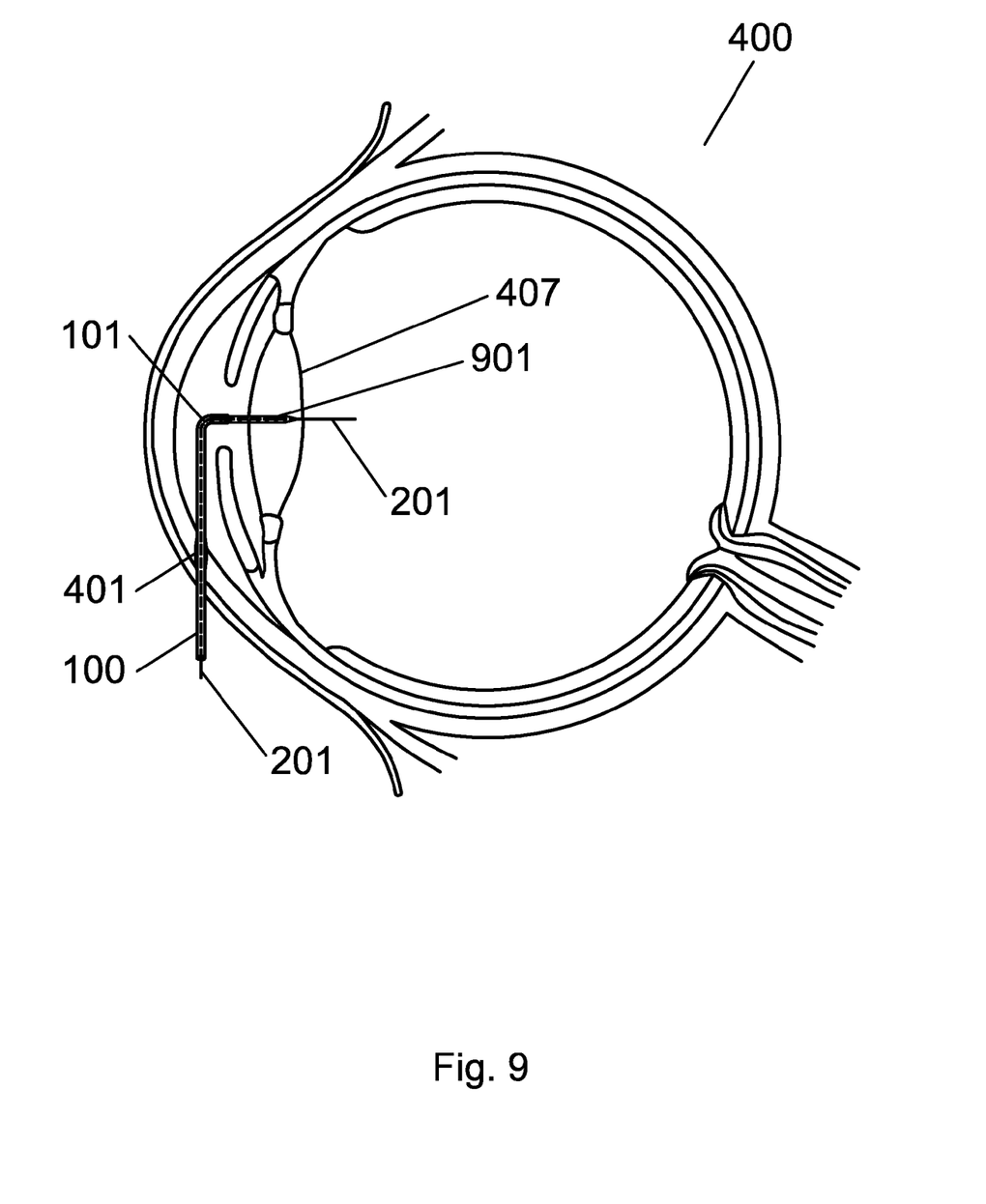
FIG. 9 is a cross sectional view of an eye showing the lens system device being deployed.

In FIG. 9, once the initial hole, passageway lumen or small tunnel is created in the lens, a stent assembly, or lens system 901 or similar structure is conveyed to or through the smaller lumen along the wire using guiding techniques such as guiding structures and the like. Or, the guiding structure could simply advance the lens or stent system primarily into the cataractous lens so it can be deployed. This guiding structure 201 may also consist of release mechanisms such as a double barrel design whereby the inner guiding structure is used to advance the lens piercing and/or lens device system into the cataract, and the outer portion is able to place counter traction on the lens device system, stent, or lumen such that the guiding structure can be removed, pulled away, and/or separated from the lens device system, stent, or lumen, and the in situ cataract without dislocating or otherwise destabilizing the new integrated relationship between cataract and lens device system, stent or lumen. Release mechanisms different from the double barrel design are other embodiments of this invention. Such release systems would allow for the separation of the guiding structure and lens device structure via severing the guiding structure from the stein or lens device system anteriorly or proximal to the lens device system or stent. Methods to accomplish this separation include but are not limited to a triggered release system activated mechanically through, for example, a fine wire, or though a micromachine or microelectromechanical system that can be turned on by a remote electromagnetic signal, or by a heat or electrically activated release mechanism whereby the portion of the guiding structure just proximal to the lens device system or stent is designed to melt, break, or become extremely weak to axial motion following activation. Thus, the lens device, system, lumen, expandable tubular lens, or stent could be left in place in the cataract after deployment or placement (and subsequent removal of the surgical tool or guiding structure from the eye) with minimal additional tissue trauma thereby reducing risks of lens subluxation, dislocation, or damage. The diameter of the initial piercing of the lens creating the pinhole, lumen, or tunnel, at first is typically between one and two millimeters, but may be between 0.10 mm. and 5 mm. In some embodiments, the cornea may also be entered from the peripheral cornea using a guiding surgical tool depicted in FIG. 1 that may have memory to bend, redirect the guide, catheter, wire, insertion system and lens system device posteriorly through the lens so that the eye need not be entered through the central cornea. In such a case, there would be a small corneal incision made with a separate blade or needle, and then the lens device system/guiding structure with curvature memory could be advanced into the eye, or the straight guiding structure/lens device deployment system apparatus with memory for curvature may penetrate the outer cornea directly with a sharp tip. There may be a secondary aspect to such a straight placement system such that an outer shell, sleeve or double barrel system allows for the memory or curvature to become manifest following the retraction or removal of the outer shell, sleeve or outer hollow barrel. The stent or lens system device 301 is placed in or near the visual axis of the eye. In some embodiments of the present invention, the stent or lens system device 301 is placed outside the visual axis of the eye, but is still able to improve sight. In some embodiments of the present invention, the lens system device, stent, small diameter cannula or other pinhole device may be mechanically forced through the cataractous lens using a mechanical system such as a spring loaded mechanism or screw/threaded rotational mechanism or the like. A mechanism to force insertion of the lens system device, stent or other pinhole device may also be electrically or battery powered, and may, in some embodiments, include a hand powered, mechanical or electrical system to drive the lens system device, tubular lens, stem or other pinhole device carefully through the lens. The mechanical energy system aspect of the device may utilize heat energy, ultrasound, laser, cautery, ionization, or other electromechanical energies to ease placement through the cataractous lens. Such mechanisms may also be used, in some embodiments of the present invention, to help drive the guide wire through the lens. In this described procedure, the pupil may be dilated or may be undilated. The procedure may be used with viscoelastic materials or without, and may include, in some embodiments of the present invention, a self healing incision. An irrigation system may be a part of the device or the deployment system of the present invention in some embodiments of the present invention. Some embodiments of the present invention may include an intraocular lens within the stem assembly 901. The intraocular lens is placed through the cataract, without removing the cataract. The intraocular lens will have a small diameter optic, for example, less than 4 mm. The lens may be flexible, expandable, or rigid, and may be preloaded in the surgical end of the operative tool or the operative end of the tool and then subsequently advanced through the bend in the tool during use. The same concept applies to any stem or lens system device that may be deployed by the apparatus—it may be preloaded in the surgical or operative end of the tool, or it may be secondarily advanced over a guide wire or secondarily placed with a separate guiding structure. Furthermore, after creating the opening through the cataract, a piggy back intraocular lens, or larger optic may be placed in the anterior chamber or in the anterior segment in front of the cataract but behind the iris to help focus light on the retina. The human lens, for reference, is 9 mm. in diameter and 4 mm. thick. Standard optics used in cataract surgery have an optic diameter between 6 mm and 4 mm. In some embodiments of the present invention, the stent may be conical with the anterior opening larger than the posterior opening. A wide angle lens to allow for a larger field of view on the retina may be utilized in this system. The stent or intraocular lens may, in some embodiments of the present invention, have a flexible flange on the lead end and trailing end of the stent, tubular lens, or lens device system to help secure it in position, enhance integration with the in situ lens capsule, and prevent egress of cataractous material. The intraocular lens may further, in some embodiments of the present invention, be telescoping. The lens system device may come in various powers to optimally correct for refractive error.

Figure 10:
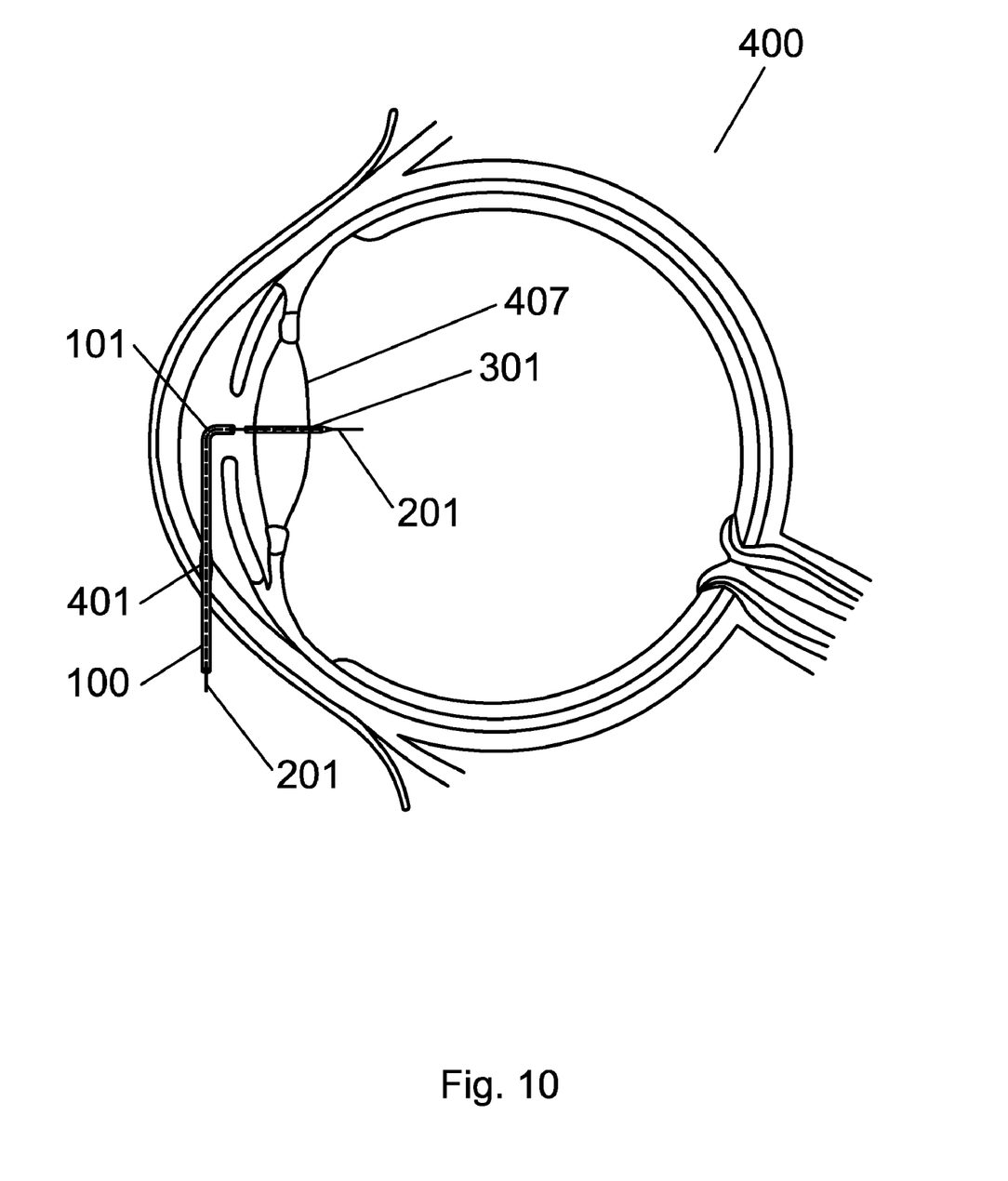
FIG. 10 is a cross sectional view of an eye showing the lens system device in position.

In FIG. 10, the lens system device 301 is properly positioned in and through the cataract, and the guiding structure 201 is retracted through the surgical tool 100. These methods may be performed by a physician or a non-physician under topical, local, or general anesthesia. The methods may be performed with or without the use of viscoelastic material or balanced saline irrigation. The lens system device 301 (including such devices as stents, cables, cannulas, catheters, a clear tunnel, intraocular lens systems, tubular lenses, expandable lenses, or polymer lenses) extends through the entire lens of the eye. The length of this stem, cable, new lumen, lens system, or material can extend 3 mm in front of the anterior surface of the lens and up to 18 mm posterior to the posterior capsule of the lens. Typically the length will extend 0.5 to 2 mm anteriorly and 0.5 to 3 mm posteriorly through the lens.

Figure 11:
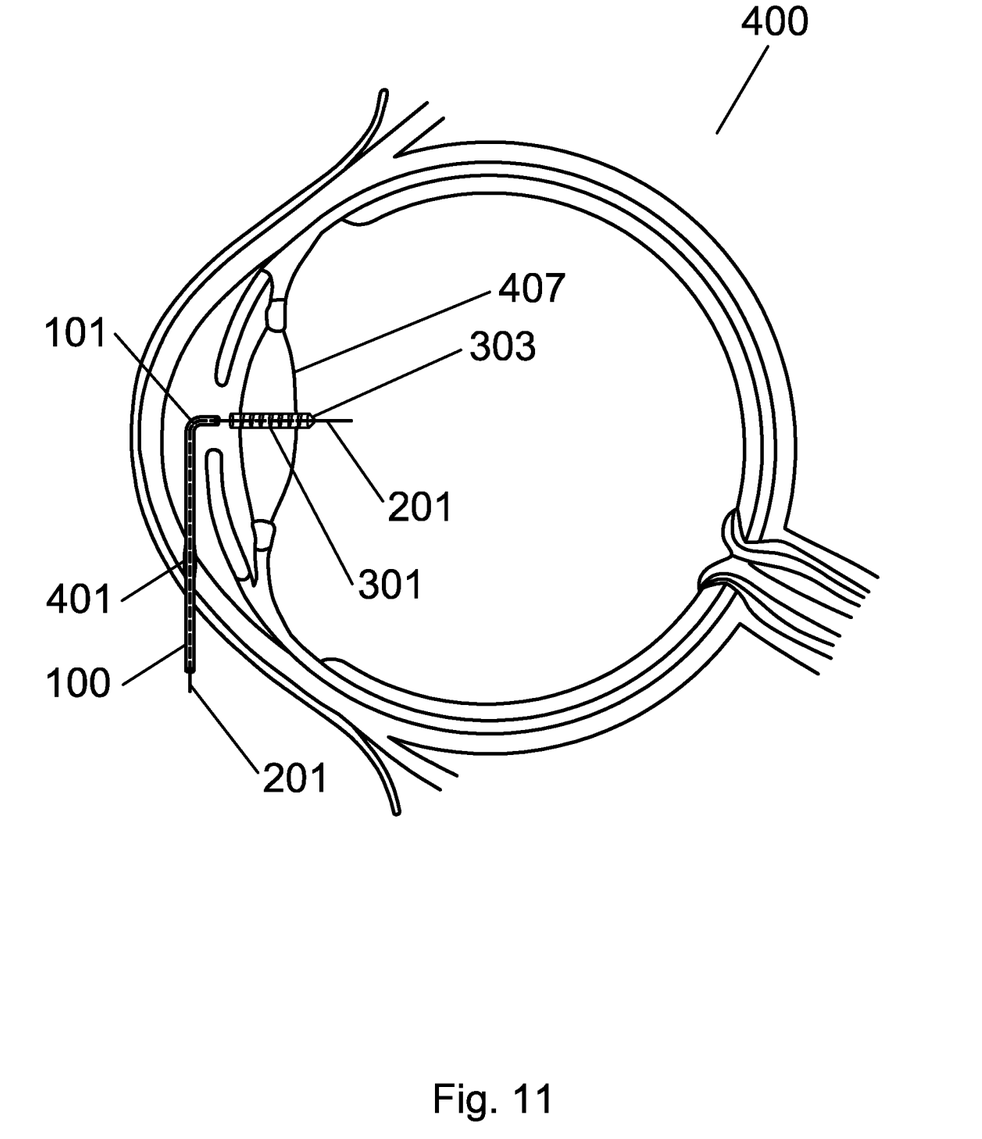
FIG. 11 is a cross sectional view of an eye showing the lens system device expanded.

FIG. 11 depicts the lens system device 301 after expansion, or the way a nonexpandable cannula will appear. Techniques to expand a stem are well known to those skilled in the art, and include self expanding stents, expansion by a balloon mechanism, and the like. The lens system device 301 after expansion creates a lens, passageway for light, or patent lumen in the lens of a mammal. In one embodiment, the stent or cannula system is non expandable. In another, it is expanded to 2 mm in diameter, up to 4 mm in diameter. The lens system device may also be made from a hydrophilic material that expands upon placement in an aqueous environment such as an eye. Suitable hydrophilic materials may include, but are not limited to, Hema (Poly-hydroxy-ethylene thacrylate), 2-hydroxyethyl methacrylate (HEMA), hydrophilic acrylic, 2 HEMA hydrophilic acrylic, hydrogels, hydrophilic polymers, fluorocarbon-sulfone.

Figure 12:
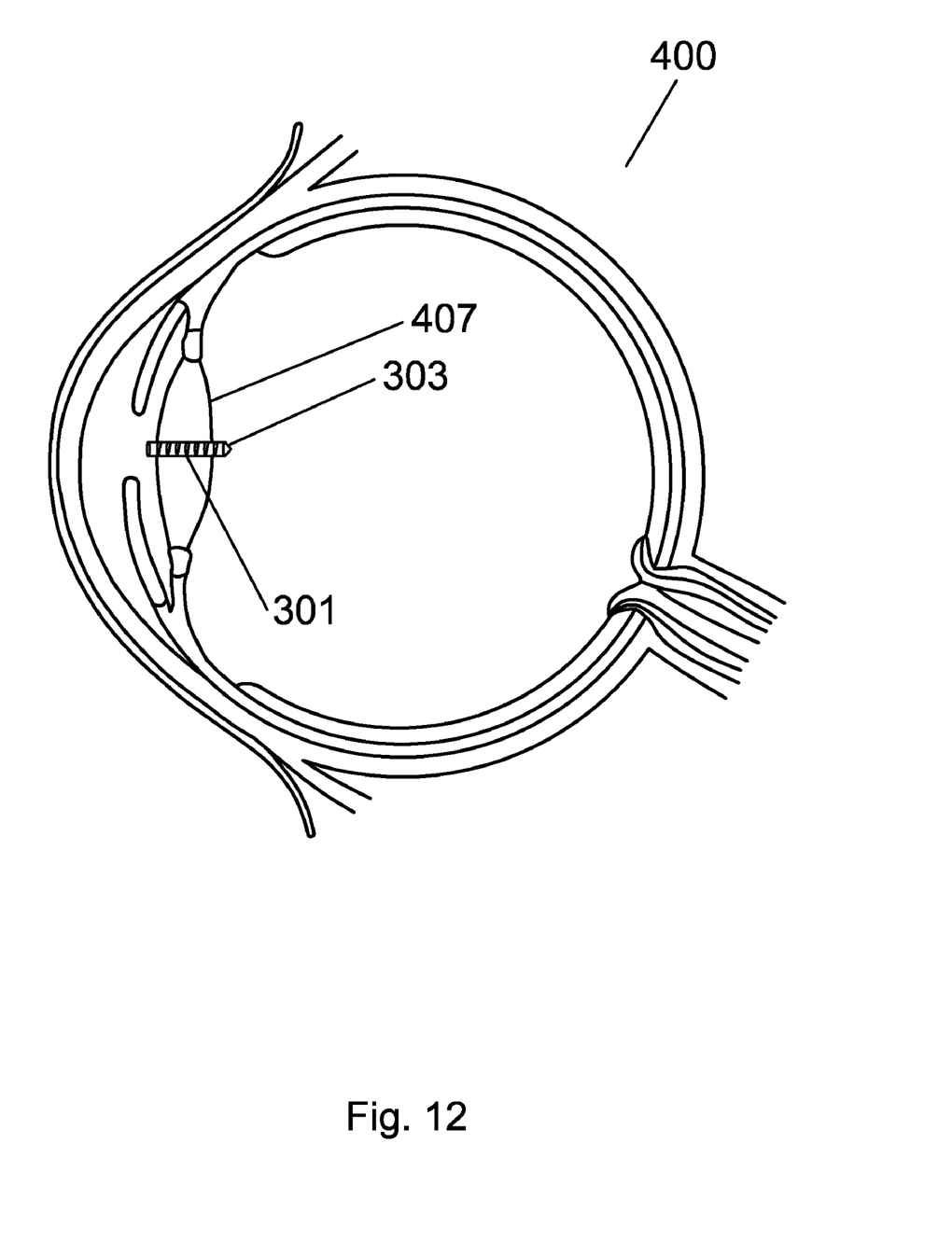
FIG. 12 is a cross sectional view of an eye showing the lens system device in place with the guide wire removed.
Figure 13:
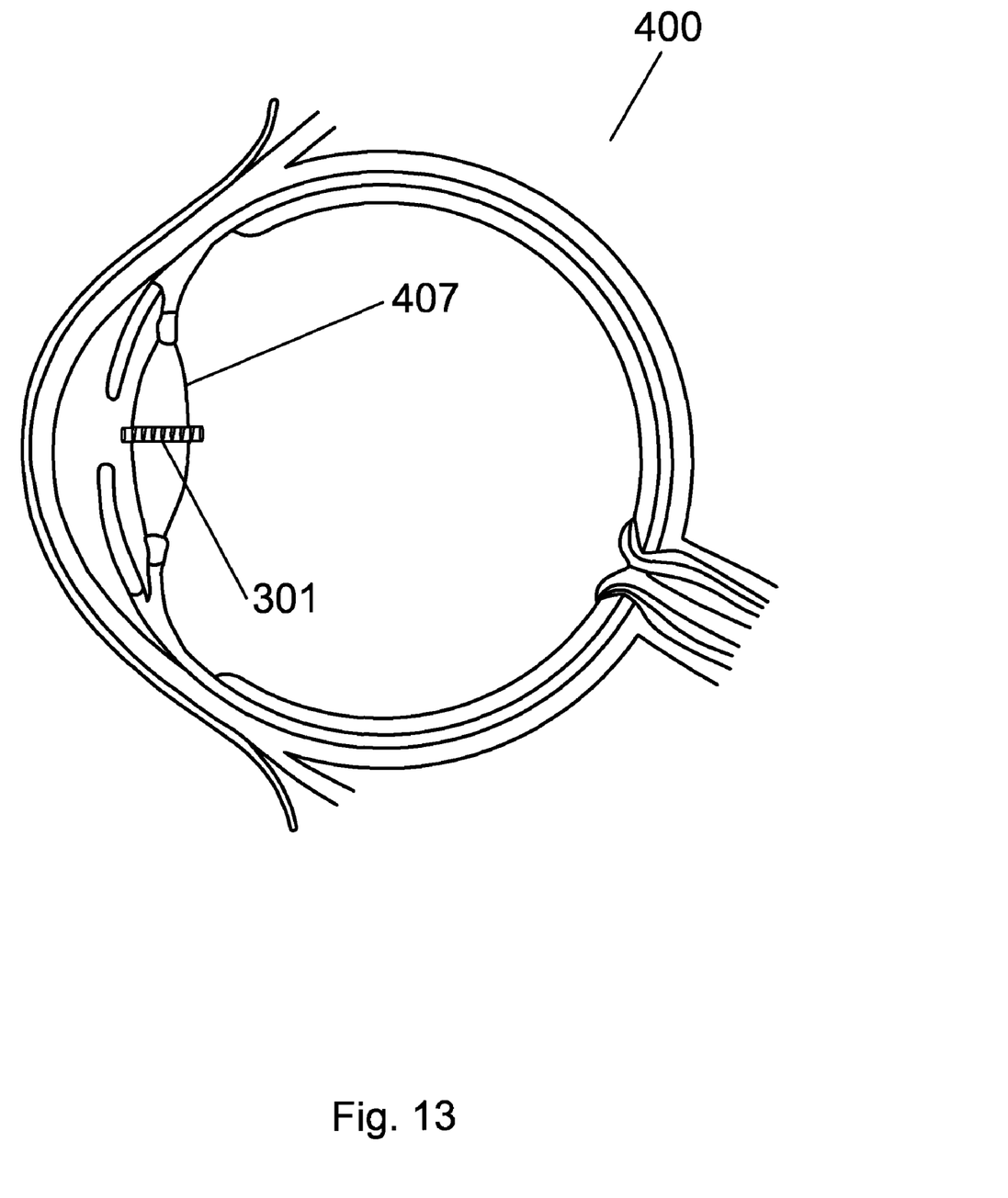
FIG. 13 is a cross sectional view of an eye showing a second embodiment of the lens system device in place with the guide wire removed.

FIG. 12 shows the lens system device 301 fully installed, with the related surgical tools removed. In FIG. 12, the lens system device 301 has a taper 303. Other embodiments of the present invention may have a modified taper, or no taper, such as depicted in FIG. 13. The taper, and/or the external surface of the stem, tubular lens, or lens system device, may have threads to assist its deployment into the cataractous lens, and the tapered aspects may convey other mechanical advantages.

Light ray tracing analysis shows that a reasonable image can be formed on the retina using an intraocular pinhole system, and one embodiment of this invention is an intra-cataract pinhole intraocular lens system.

It is, therefore, apparent that there has been provided, in accordance with the various objects of the present invention, an apparatus and method for the treatment of cataract. While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the present invention and the various embodiments described and envisioned by this specification, claims, and attached drawings.

What is claimed is:

1. An apparatus for treating a cataract of an eye, comprising:
a surgical tool formed with an angle to allow entry of the surgical tool through the peripheral cornea of the eye, the angle within sixty degrees greater or less than ninety degrees, the angle creating a longer operative end of the surgical tool and a shorter surgical end of the surgical tool;
the shorter surgical end of the surgical tool allowing for penetration of the peripheral cornea of the eye;
a lens system device contained within the surgical tool; and
a guiding structure attached to the lens system device and further slidably disposed within the surgical tool; said guiding structure having a flexibility that makes it capable of traveling through an angle of ninety degrees.

2. The apparatus for treating cataract of an eye of claim 1, wherein the lens system device is a stent.

3. The apparatus for treating cataract of an eye of claim 2, further comprising a stem expansion device.

4. The apparatus for treating cataract of an eye of claim 1, wherein the lens system device is an expandable hydrophilic device.

5. The apparatus for treating cataract of an eye of claim 4, wherein the expandable hydrophilic device is made from a material selected from the group consisting of poly(2-Hydroxyethylmethacrylate) (pHEMA), hydrogels, and hydrophilic polymers.

6. The apparatus for treating cataract of an eye of claim 1, wherein the lens system device further comprises a taper.

7. The apparatus for treating cataract of an eye of claim 1, further comprising a drug eluting coating disposed on the lens system device.

8. The apparatus for treating cataract of an eye of claim 6, wherein the taper of the lens system device is detachable.

9. The apparatus for treating cataract of an eye of claim 1, wherein the lens system device further comprises an intraocular lens.

10. The apparatus for treating cataract of an eye of claim 1, wherein the lens system device further comprises a coating selected from the group consisting of poly(methyl methacrylate), poly(ethylene-co-vinyl alcohol), poly(butyl methacrylate), polyglycolic acid, poly(L-lactic acid), a copolymer, nylon, drug eluting polymeric systems, hydrophobic polymers, hydrophilic polymers, polyethylene terephthalate and carbon nanotubes.

11. The apparatus for treating cataract of an eye of claim 1, wherein the lens system device has a diameter in the range of from about 1 mm, to about 5 mm.

12. The apparatus for treating cataract of an eye of claim 1, wherein the lens system device further has a midsection diameter smaller than the average diameter of the lens system device.

13. The apparatus for treating cataract of an eye of claim 1, further comprising a device providing a source of energy.

14. The apparatus for treating cataract of an eye of claim 13, wherein the device providing a source of energy is selected from the group consisting of a device providing ultrasonic energy, a device providing laser energy, a device providing thermal energy, a device providing electrical energy, a device providing ionization energy, a device providing chemical energy, a device providing nuclear energy, a device providing optical energy, a device providing mechanical energy, a device providing spring loaded energy, and a device providing rotational energy.

15. The apparatus for treating cataract of an eye of claim 1, wherein the surgical tool is made from a material selected from the group consisting of stainless steel, titanium, metal, ceramic, glass, plastic, and polymer.

\* \* \* \* \*